United States Patent [19]

Toyama

[11] Patent Number: Plant 7,045

[45] Date of Patent: Oct. 10, 1989

[54] APRICOT TREE PA 7201-1

[75] Inventor: Thomas K. Toyama, Prosser, Wash.

[73] Assignee: Washington State University Research Foundation, Pullman, Wash.

[21] Appl. No.: 222,576

[22] Filed: Jul. 21, 1988

[51] Int. Cl.[4] ..... A01H 5/02

[52] U.S. Cl. ..... Plt./39

[58] Field of Search ..... Plt. 39

*Primary Examiner*—Robert E. Bagwill

*Attorney, Agent, or Firm*—Chernoff, Vilhauer, McClung & Stenzel

[57] ABSTRACT

A new variety of apricot tree bearing fruits of very large size, good quality and flavor and exceptional firmness. The fruits of this new variety are characterized by its attractive light orange color overlayed by a reddish purple blush. Its firm, large-sized fruits have long storage and shelf life and are particularly adapted to premium, long-distance fresh markets.

2 Drawing Sheets

BACKGROUND AND SUMMARY OF THE INVENTION

The present invention relates to a new and distinct variety of apricot tree which bears large to very large, firm, attractive fruits of excellent quality and flavor. The fruit is especially well adapted for shipment for fresh markets because of its firmness, long shelf life and excellent dessert quality.

This new variety of apricot tree was originated at the Irrigated Agricultural Research and Extension Center at Prosser, Wash. from crosses made in 1972. It was selected in 1976 from 92 seedlings of the cross Goldrich X Blenril (both varieties unpatented). Second test trees were planted on the Roza unit of the Center in 1977 and came into production in 1980.

Flowers of the present variety require cross-pollination. They will set fruits with pollen of one of their parents (the Goldrich variety) and with Perfection (unpatented). In addition, flowers of the subject variety are pollinated by and will pollinate flowers of Apricot Tree PA 7221-1 which is the subject of a patent application filed concurrently herewith.

In the Yakima valley the fruits of this variety ripen about two weeks before that of Wenatchee (unpatented). The round to oval-shaped fruits have slightly compressed sides and are very large being up to $2\frac{3}{4}$ inches in diameter when adequately thinned. The skin is light orange with a reddish purple blush covering up to 30% of the surface. It is slightly glossy in appearance. The flesh is very firm and moderately juicy. Some acidity is associated with the skin. Fresh market quality is rated as excellent whereas canning quality is poor, becoming mushy when canned. The fruit most nearly resembles that of variety PA 7221-1. These two new apricot varieties are meant to be planted together in the orchard as sister varieties since they cross pollinize one another and produce similar fruits which mature at the same time. Thus, the fruits can be harvested, packed and shipped together.

Trees of the subject variety are vigorous on the common rootstocks used for apricot trees. They bloom heavy but often tend to set relatively light crops thereby reducing the need for thinning. The extra large attractive fruits can readiy be tradepacked for premium fresh markets.

Asexual reproduction of this new and distinct variety shows that its unique characteristics come true to form and are established and transmitted through succeeding propagations by grafting.

BRIEF DESCRIPTION OF THE DRAWINGS

In the accompanying photographs, vegetative growth and fruit of the new variety are shown both on and off the tree and are depicted in color as nearly true as is reasonably possible to make in color illustrations of this character:

FIG. 2 shows the stems and leaves along with the whole and half fruits of the subject variety off of the tree.

DETAILED DESCRIPTION OF THE DISCLOSURE

Figure 1:
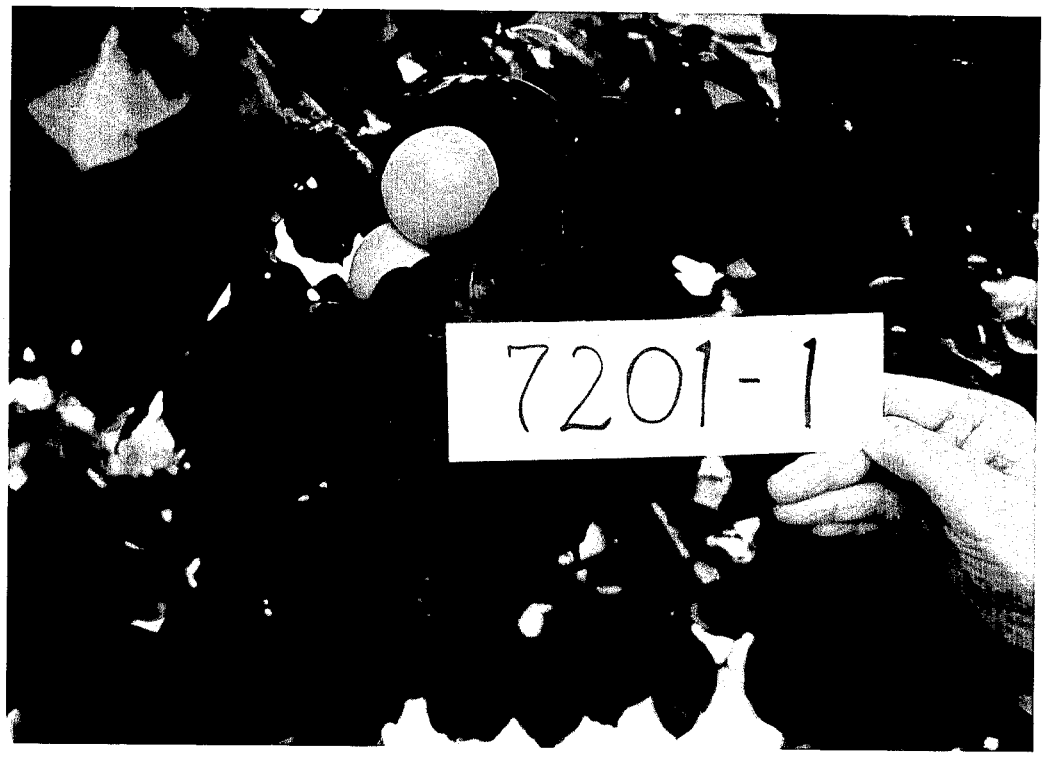
FIG. 1 shows the vegetative growth and fruit of a mature specimen of the subject variety on the tree.

The following description was based on observations made of four six-year-old second generation trees growing at the Irrigated Agriculture Research Station at Prosser, Wash. and of three five-year-old trees growing in a variety test plot at Parker, Wash. Color designations are to Munsell Color Cascade Chart except where general color terms of ordinary dictionary significance are used.

Tree:
- *Size.*—Large.
- *Growth.*—Upright, then spreading.
- *Production.*—Productive.
- *Vigor.*—Vigorous.
- *Density.*—Medium dense.
- *Bearing.*—Regular.

Trunk:
- *Size.*—Stocky.
- *Texture.*—Medium.

Branches:
- *Size.*—Medium stocky
- *Texture.*—Medium smooth.
- *Lenticels.*—Medium size, numerous.
- *Color.*—Dark brown (29-15) to reddish brown (30-14).

Leaves:
- *Size.*—Large, average length $3\frac{1}{4}$ inches to $3\frac{7}{8}$ inches, average width $2\frac{7}{8}$ inches to $3\frac{3}{4}$ inches.
- *Shape.*—Ovate, pointed.

*Petiole.*—Medium length, medium thickness.

*Glands.*—Usually two on blade and two to six on petiole, alterate, globose, green.

*Margin.*—Crenate, finely serrate.

*Color.*—Upper surface — green (20-12), lower. surface — light green (20-10).

Flower buds:

*Size.*—Medium to large.

*Shape.*—Conical.

*Length.*—Medium.

*Surface.*—Lightly pubescent.

Flowers:

*Date of bloom.*—Full bloom, March 26.

*Size.*—Large.

*Color.*—Link pink to almost white when open with reddish sepals.

*Pubescence.*—Slight.

*Number of pistils.*—One.

*Number of stamens.*—Average 26 to 30.

Fruit:

*Maturity.*—About 14 days before Wenatchee, about July 10 at Prosser, Wash. and about July 13 at Parker, Wash.

*Size.*—Uniformly large, diameter — $2\frac{1}{2}$ inches to $2\frac{3}{4}$ inches, transverse in suture plane — $2\frac{1}{2}$ inches to $2\frac{3}{4}$ inches, transverse at right angles to suture plane — 2 inches to $2\frac{1}{2}$ inches.

*Form.*—Slightly compressed sides, uniform, only slight lateral compression towards suture, round to oval.

*Suture.*—Distinct, extends from base to apex.

*Cavity.*—From rounded to slightly elongated in suture plane, shallow $\frac{1}{4}$ inch, average breadth $\frac{1}{2}$ inch.

*Base.*—Rounded to slightly retuse, smoothly rounded on dorsal side, abruptly rounded on suture side.

*Apex.*—Rounded.

*Pistil point.*—Slightly depressed.

*Stem.*—Length 3/16 inch, caliper $\frac{1}{8}$ inch.

*Skin.*—Medium thickness, smooth, glossy, medium texture. Tendency to crack: None. Down: Very short, scant. Color: Light orange ground (32-8), reddish purple blush (43-12) on portion of fruit exposed to sun. Tenacity: Tenacious flesh.

Flesh:

*Uniformity.*—Uniform ripening only slightly earlier at apex.

*Texture.*—Very firm, meaty, fine grained.

*Surface of pit cavity.*—Smooth.

*Juice.*—Slightly juicy.

*Flavor.*—Sweet, strong flavor distinction, subacid.

*Aroma.*—Pleasing, aromatic.

*Color.*—Normal apricot (30-7).

*Eating quality.*—Very good.

Stone:

*Type.*—Free stone.

*Size.*—Large, average length $1\frac{1}{4}$ inches, average breadth $1\frac{1}{8}$ inches, average thickness $\frac{5}{8}$ inch.

*Form.*—Ovate, slightly flattened at base and slightly pointed at apex.

*Sides.*—Slightly pitted.

*Dorsal suture.*—Full, with deep broad groove.

*Color.*—From light brown (28-12) to brown (28-14).

*Tendency to split.*—None.

Use: Fresh, local and long-distance markets.

Keeping Quality: Very good.

Shipping Quality: Very good.

What is claimed is:

1. A new and distinct variety of apricot tree obtained as a seedling from a seed parent entitled Goldrich (unpatented) and a pollen parent entitled Blenril (unpatented) is characterized by its large to very large firm attractive fruits of excellent quality and flavor which are especially well adapted for shipment to fresh markets because of its firmness, long shelf life and excellent dessert quality, substantially as shown and described.

* * * * *

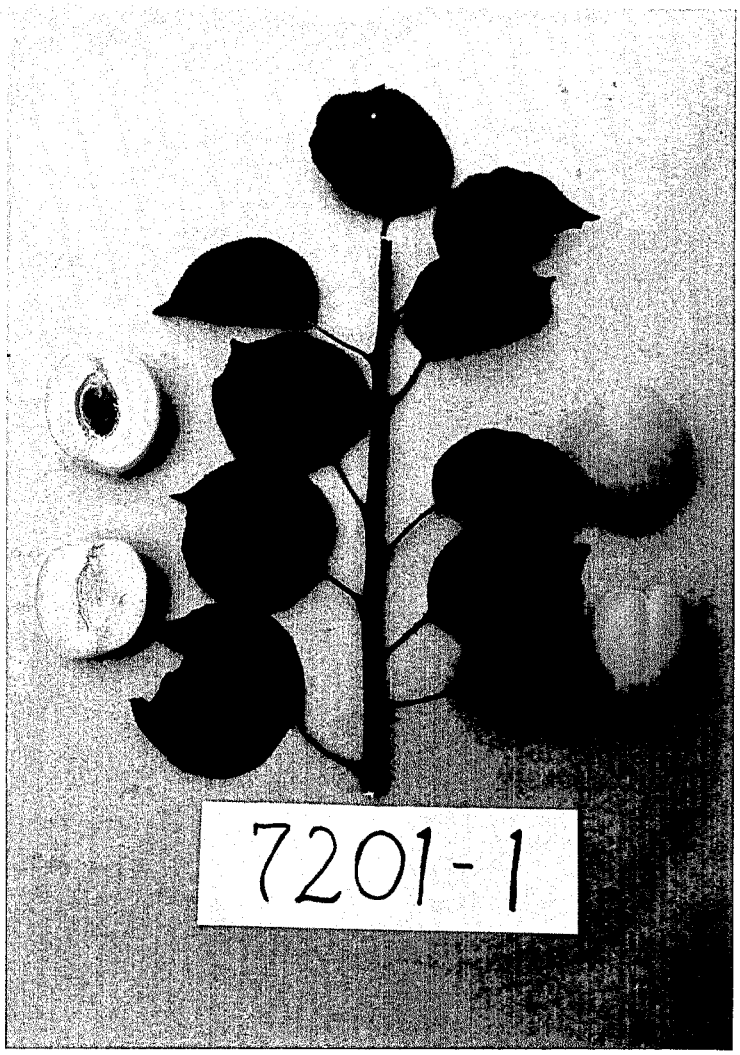
7201-1